United States Patent [19]
Yeatts, II et al.

[11] Patent Number: 5,968,054
[45] Date of Patent: Oct. 19, 1999

[54] COMPRESSIBLE STRUCTURE CLAMPING AND CUTTING

[76] Inventors: Stanley D. Yeatts, II, 134 Chinquapin Orchard, Yorktown, Va. 23693; Michael J. Palmer, 17 Alphus St., Poquoson, Va. 23662

[21] Appl. No.: 09/022,061

[22] Filed: Feb. 11, 1998

[51] Int. Cl.[6] .................................................. A61B 17/42
[52] U.S. Cl. ........................... 606/120; 606/167; 606/151
[58] Field of Search ..................................... 606/119, 120, 606/151, 157, 167

[56] References Cited

U.S. PATENT DOCUMENTS

| | | | |
|---|---|---|---|
| 4,428,374 | 1/1984 | Auburn | 606/120 |
| 5,676,672 | 10/1997 | Watson et al. | 606/120 |
| 5,797,922 | 8/1998 | Hessel et al. | 606/120 |
| 5,817,103 | 10/1998 | Bell | 606/120 |

*Primary Examiner*—Glenn K. Dawson
*Attorney, Agent, or Firm*—Peter J. Van Bergen

[57] ABSTRACT

A device and method are provided for clamping and severing a compressible structure containing a fluid. A clamp having a pair of arms is secured in a clamped position about the structure so that the fluid between the arms is forced outward therefrom. A cutting assembly coupled to the clamp cuts through the pair of arms while in the clamped position to form first and second separated clamps that remain in the clamped position. As a result, the structure is severed and clamped without fluid discharge.

27 Claims, 5 Drawing Sheets

COMPRESSIBLE STRUCTURE CLAMPING AND CUTTING

FIELD OF THE INVENTION

The invention relates generally to clamping and cutting devices, and more particularly to a device and method for clamping and cutting a compressible structure such as an umbilical cord.

BACKGROUND OF THE INVENTION

The severing of a fluid-filled compressible structure typically involves fluid loss from one or both sides of the severed structure. In most instances, the fluid loss is not desirable. Accordingly, some form of clamping of the structure takes place prior to the severing thereof. One example of this is the umbilical cord of a newly-delivered baby which must be severed shortly after delivery. For years, this process has been accomplished by clamping the cord at two separated positions therealong. The physician, father or other attendant then cut the cord between the two clamps. The limitations or drawbacks of this process are related to the convenience, speed and safety of the process.

In terms of convenience, three separate motions are required to clamp (twice) and then sever the umbilical cord. Further, a separate instrument must be handled by each motion thereby increasing the number of instruments that must be accessible on an instrument tray. In terms of speed, each separate motion requires valuable seconds at a time when even one or two seconds can be critical to the newborn's well-being. In terms of safety, the umbilical cord between the two separated clamps is under increased hydrostatic pressure. Thus, regardless of how little a gap there is between the two clamps, blood can be sprayed indiscriminately when the cord is cut. With today's concerns over blood-borne pathogens (e.g., HIV, Hepatitis viruses, etc.), even a little blood discharge can be a problem for physicians, nurses and all other people present at the delivery.

In efforts to improve the process of cutting the umbilical cord, a variety of clamping and cutting devices have been developed. For example, in U.S. Pat. No. 4,716,886, a hand-held device includes two clamps that are held together in a side-by-side relationship by a shear pin. A cutting blade located between the two clamps is used to cut the cord clamped by the two clamps. The single device clamps and cuts with the same motion thereby addressing the convenience and speed issues outlined above. However, safety is still a concern as the gap between the two clamps contains blood under pressure that will be discharged when the cord is cut.

In U.S. Pat. No. 5,584,840, a similar structure to that just described is disclosed. An additional feature includes splash guards to prevent blood from splashing in the direction of surrounding individuals. While the safety concern is addressed in that the indiscriminate spraying of blood is prevented, the fact remains that blood will be discharged when the umbilical cord is cut.

SUMMARY OF THE INVENTION

Accordingly, it is an object of the present invention to provide a device and method for clamping and cutting a compressible structure such as an umbilical cord.

Another object of the present invention is to provide a device and method for clamping and cutting a compressible structure containing a fluid that prevents the discharge of any of the fluid as the compressible structure is cut.

Other objects and advantages of the present invention will become more obvious hereinafter in the specification and drawings.

In accordance with the present invention, a device and method are provided for clamping and severing a compressible structure containing a fluid. A clamp having a pair of arms is securable in a clamped position about a compressible structure containing a fluid so that the fluid between the arms is forced outward from the clamp. A cutting assembly coupled to the clamp cuts through the pair of arms while in the clamped position to form first and second separated clamps that remain in the clamped position. As a result, the compressible structure is severed to form first and second severed ends thereof clamped by a respective one of the first and second separated clamps.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein.

DETAILED DESCRIPTION OF THE INVENTION

Referring now to the drawings, one embodiment of the clamping and cutting device will be described with simultaneous reference to FIGS. 1–4. The same reference numerals will be used when describing common elements in the various drawings. The present invention can be used to clamp and cut a compressible structure while minimizing or eliminating any fluid discharge from the severed ends of the compressible structure. By way of example, the present invention will be described for its use in the clamping and cutting of an umbilical cord. However, the present invention could also be used to clamp and cut a variety of fluid-filled compressible structures or hoses used in medical, biochemical or industrial applications.

Figure 1:
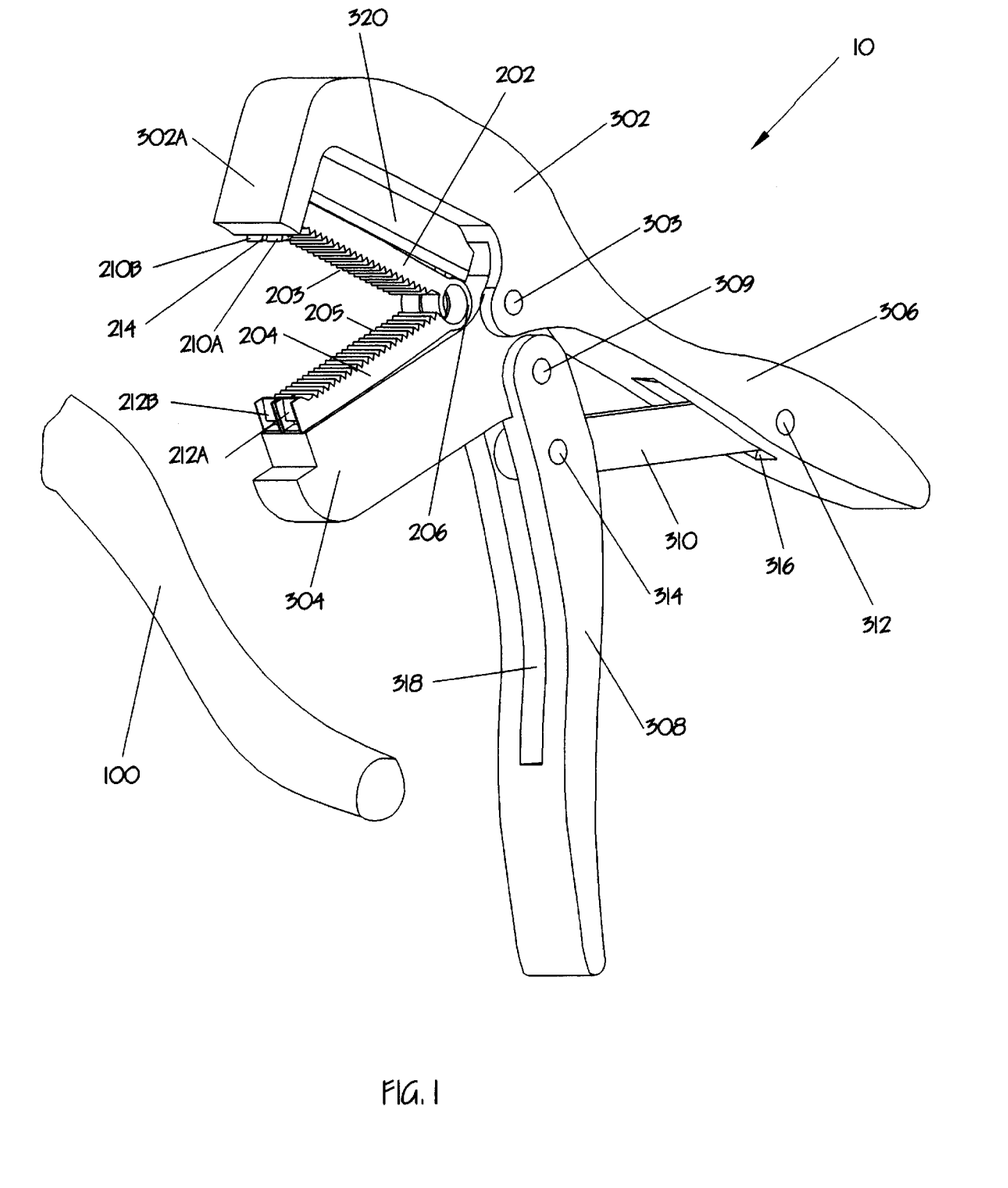
FIG. 1 is a perspective view of the clamping and cutting device in its open or unclamped position in accordance with one embodiment of the present invention.

The entirety of the clamping and cutting device of the present invention is illustrated in FIG. 1 and referenced generally by numeral 10. In the illustrated embodiment, device 10 includes a single clamp 20 shown in isolation in FIGS. 2A and 2B. Clamp 20 is severed by the present invention to form two separate clamps 21 and 22 as shown in FIG. 4. A hand held/gripped jaw assembly 30 is shown in isolation in FIGS. 3A and 3B.

Materials used for clamp 20 and jaw assembly 30 are preferably strong and substantially rigid to be capable of transmitting sufficient force through jaw assembly 30 and clamp 20 in order to: i) clamp an umbilical cord 100, ii) cut cleanly through clamp 20, and iii) cut cleanly through umbilical cord 100 thereby leaving both severed ends thereof clamped as shown in FIG. 4. For example, most of the elements of clamp 20 and jaw assembly 30 can be fabricated from polypropylene by injection molding or other suitable fabrication processes. While clamp 20 would be made for a single use, jaw assembly 30 can be manufactured to be a single or multiple use component. In terms of its use in the cutting of an umbilical cord, clamp 20 and jaw assembly 30 must be sterilized prior to use in ways well known in the art.

Figure 2A:
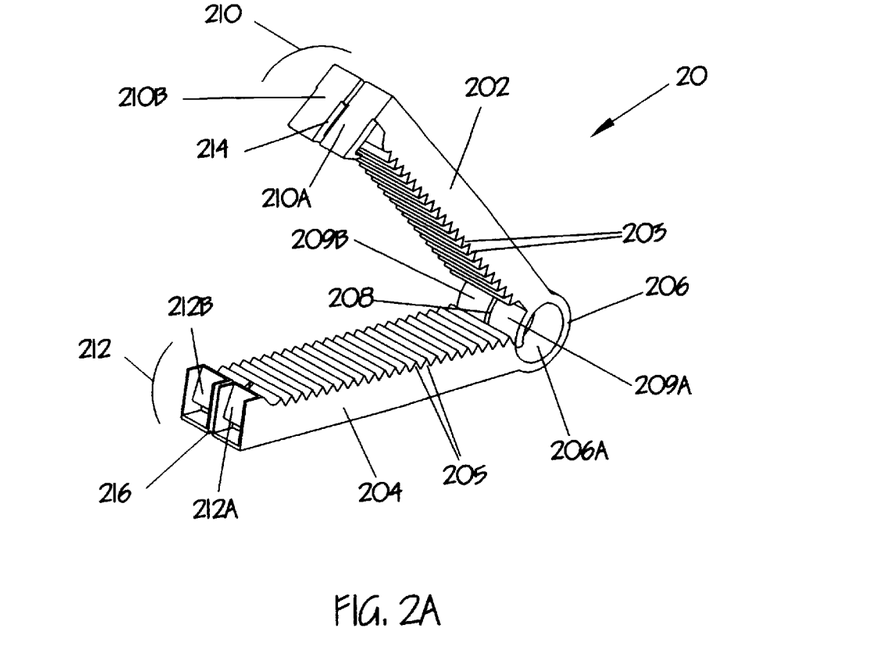
FIG. 2A is a perspective view of the front side of the clamp in its open or unclamped position.
Figure 2B:
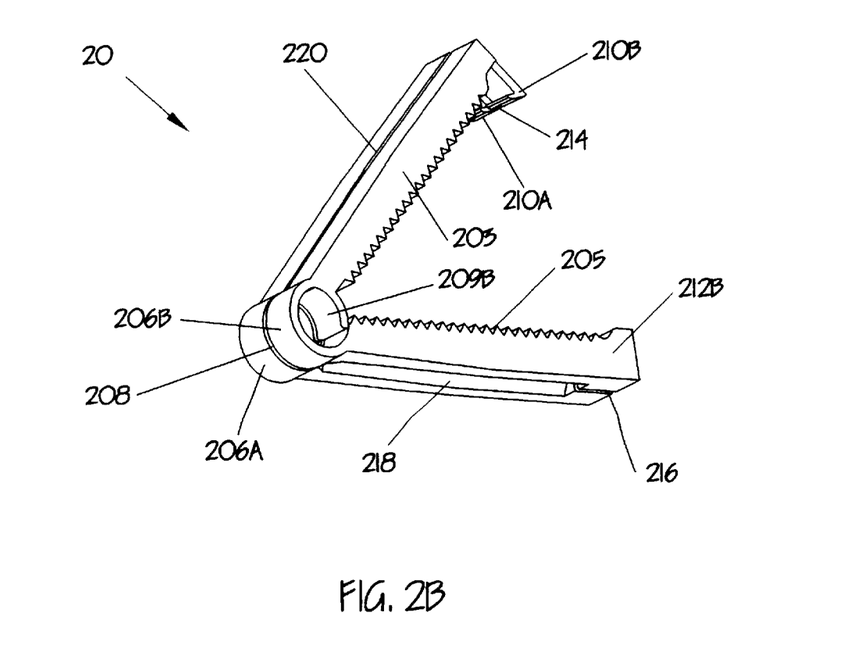
FIG. 2B is a perspective view of the backside of the clamp in the open or unclamped position.
Figure 2C:
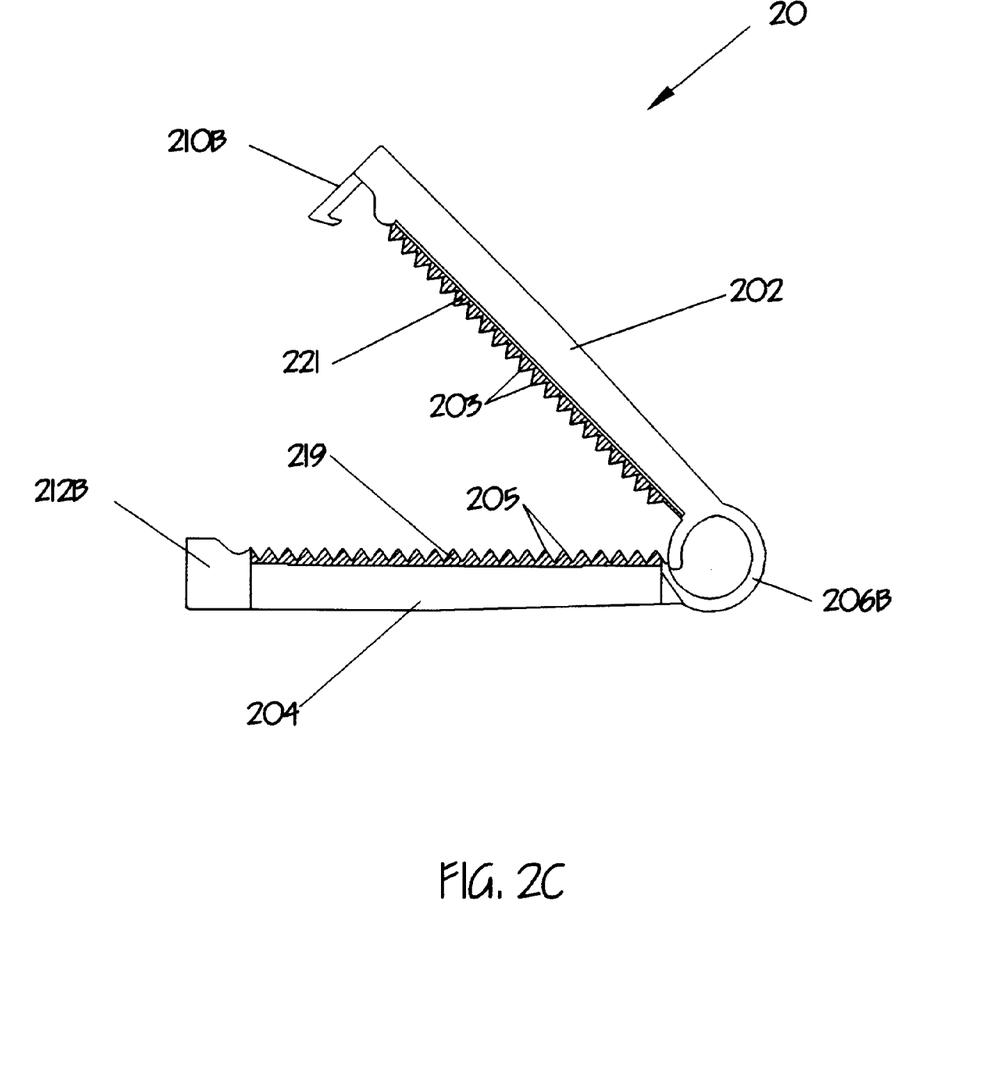
FIG. 2C is a cross-sectional view of the clamp taken through and along the central portion of the clamp to illustrate the reduced thickness portions that facilitate the severing thereof.

Referring to FIGS. 2A–2C, clamp 20 is a single clamp prior to the severing thereof. Typically, clamp 20 is of unitary construction as shown, although it could also be an assembled component. Clamp 20 has a pair of arms 202 and 204 that can be secured in a clamped position. In the illustrated embodiments, arms 202 and 204 are hinged to one another at one end of clamp 20 by a hinge 206 which can be integral with arms 202 and 204. For reasons that will become more evident later in the description, hinge 206 is constructed as a first hinge 206A and a second hinge 206B which are separated from one another by a gap 208. Hinge 206 can also be constructed to include limiting or stop tangs 209A and 209B, the presence of which prevents a compressible structure to be clamped from being pushed into, and interfering with, hinge 206.

At the opposite end of clamp 20, a latch is provided so that clamp 20 can be locked into a clamped position. More specifically, arm 202 has a latching tang 210 integral therewith while arm 204 has a latching seat 212 integral therewith. Once again, for reasons that will become more evident later in the description, latching tang 210 is constructed as a first latching tang 210A and a second latching tang 210B separated from one another by a gap 214. Similarly, latching seat 212 is constructed as a first latching seat 212A and a second latching seat 212B separated from one another by a gap 216. Accordingly, latching tang 210A and latching seat 212A combine to form a first latch while latching tang 210B and latching seat 212B form a second latch.

Between the latch (i.e., latching tang 210 and latching seat 212) and hinge 206, the opposing faces of arms 202 and 204 define clamping surfaces that can have a series of ridges 203 and 205, respectively, formed thereon such that ridges 203 interlock with ridges 205 when clamp 20 assumes its clamped position (FIG. 4). In the illustrated embodiment, ridges 203 and 205 are arranged generally parallel to one another and generally parallel to the compressible structure (not shown in FIGS. 2A–2C for sake of clarity) that will be clamped thereby. Ridges 203 and 205 span the entire width of arms 202 and 204, respectively. Ridges 203 and 205 should cover an area between the hinge and latch portions of clamp 20 at least equal to the width of the compressible structure being clamped and typically would be provided over the entire length of arms 202 and 204 between the latch and hinge portions of clamp 20.

In FIG. 2B, features of the backside of clamp 20 are illustrated. More specifically, the backside of arm 204 has a recessed portion 218 extending into and along arm 204 between hinge 206 and latching seat 212. Recessed portion 218 serves as an aid to positioning clamp 20 in jaw assembly 30. The backside of arm 202 has a narrow recess or groove 220 extending into and along arm 202 to link gaps 208 and 214. Groove 220 must be wide enough to receive a cutting blade therethrough as will be described below.

Referring now to FIG. 2C, a cross-sectional view taken along the length of clamp 20 and through the central portion of recessed portion 218 and groove 220 is presented. In arm 204, recessed portion 218 stops short of ridges 205 resulting in a reduced thickness portion 219 being defined between the tops of ridges 205 and recessed portion 218. In a similar fashion, groove 220 stops short of ridges 203 resulting a reduced thickness portion 221 being defined between the tops of ridges 203 and groove 220. The resulting reduced thickness portions 219 and 221 tie both sides of clamp 20 together. Further, reduced thickness portions 219 and 221 facilitate the severing of clamp 20 as they are aligned with one another and with gaps 208, 214 and 216.

Figure 3A:
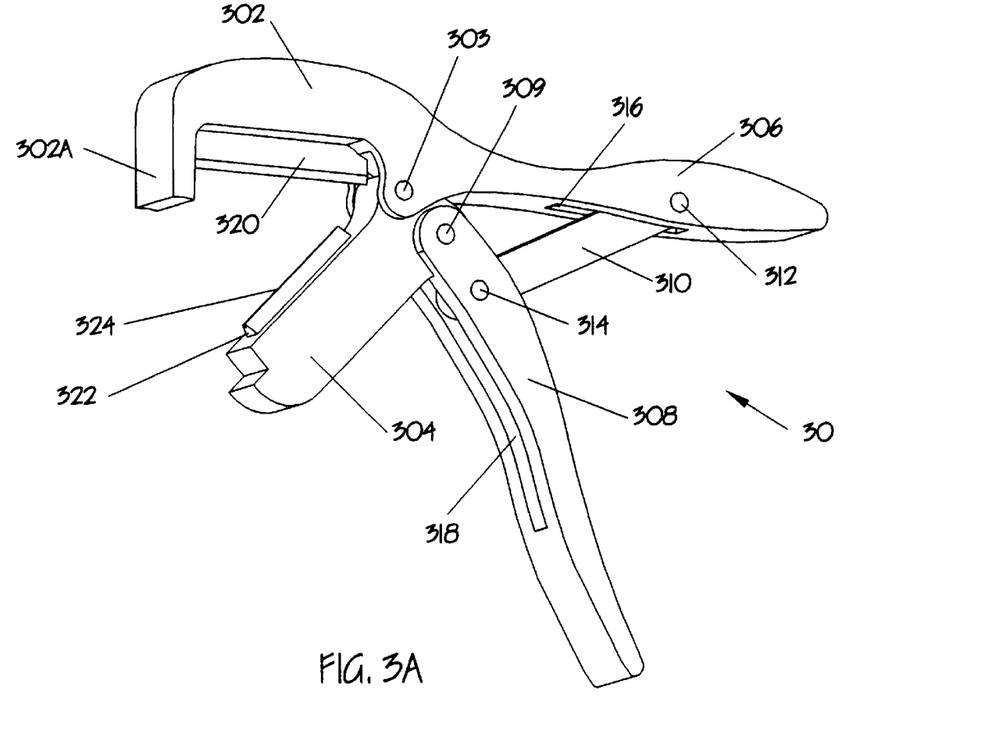
FIG. 3A is a perspective view of the jaw assembly shown in FIG. 1 in its open position without the clamp installed therein.
Figure 4:
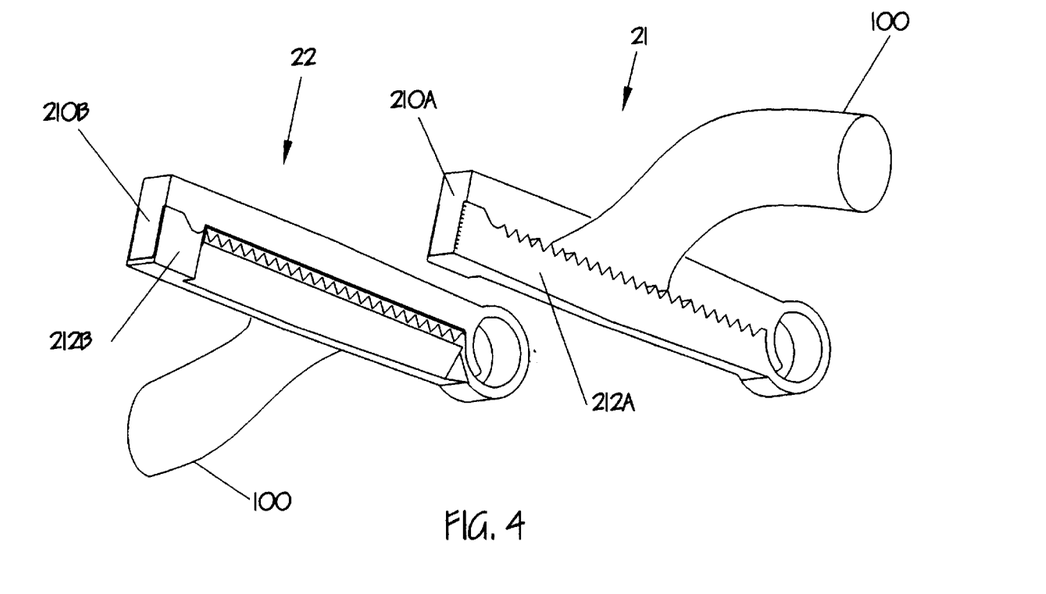
FIG. 4 is a perspective view of the clamp after it has been severed to define first and second separated clamps that remain clamped onto the severed ends of the compressible structure such as an umbilical cord.

Jaw assembly 30, shown in isolation in its open position in FIG. 3A, is presented by way of example for the purpose of: i) placing clamp 20 in its clamped position about the periphery of a compressible structure, ii) cutting through clamp 20 and the compressible structure, and iii) releasing therefrom the severed portions of clamp 20. However, it is to be understood that other types of jaw assemblies could be used without departing from the scope of the present invention.

In the illustrated example, jaw assembly 30 includes an upper jaw 302 coupled to an upper handle 306 and a lower jaw 304 coupled to a lower handle 308. Jaws 302 and 304 are hinged to one another at hinge pin 303. Upper handle 306 is fixed to or made integral with jaw 302. Lower handle 308 is pivotally coupled to jaw 304 by hinge pin 309 located beneath hinge pin 303. Upper handle 306 and lower handle 308 are coupled to one another by a leverage link 310. More specifically, leverage link 310 is pivotally coupled to upper handle 306 by hinge pin 312 and to lower handle 308 by hinge pin 314. To allow handles 306 and 308 to be squeezed together, slots 316 and 318 are provided in upper handle 306 and lower handle 308, respectively. The mechanical advantages offered by this design of jaw assembly 30 include: i) jaws 302 and 304 remain open until handles 306 and 308 are squeezed together; ii) during the initial movement of handle 308, a relatively quick closure of jaw 304 towards jaw 302 is achieved with only a small amount of movement of handle 308; iii) during later movement of handle 308, a relatively slow closure but with high force being generated between jaws 304 and 302 is achieved to cleanly sever the clamp; and iv) better control over the clamping operation than if the clamp were just squeezed together by hand.

Figure 3B:
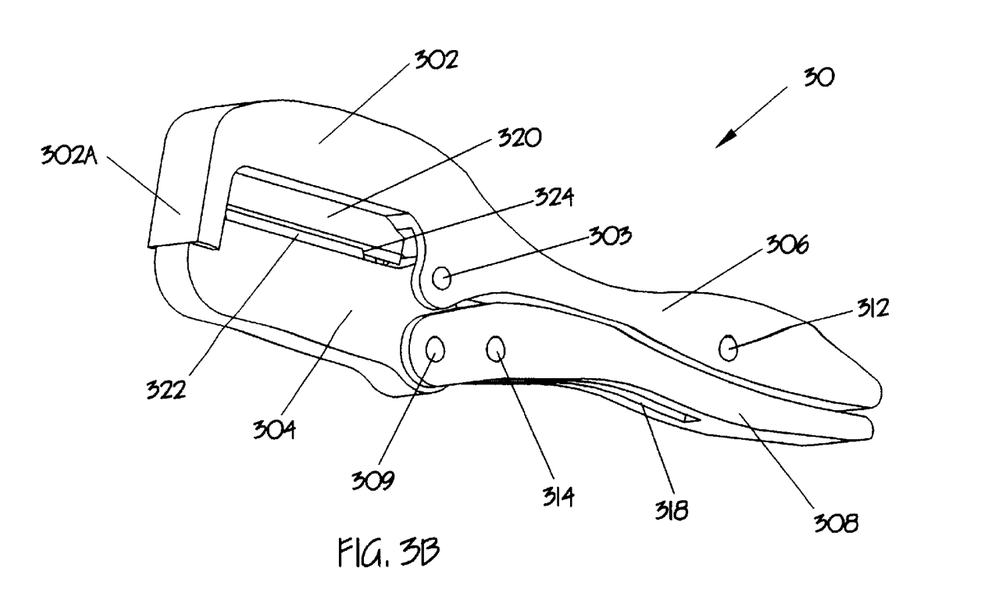
FIG. 3B is a perspective view of the jaw assembly shown in FIG. 3A in its closed position.

The opposing portions of jaws 302 and 304 cooperate with elements of clamp 20 to seat clamp 20 therein in both its open and clamped positions and to release clamp 20 therefrom after it (and the clamped compressible structure) have been severed. A cutting blade 320 is attachable or fixed therealong to jaw 302. A positioning anvil 322 is attachable to or fixed therealong to jaw 304. Blade 320 and anvil 322 are positioned such that when jaws 302 and 304 are closed as shown in FIG. 3B, blade 320 will come to rest on top of anvil 322. To maintain blade 320 in its proper orientation as jaws 302 and 304 are closed, anvil 322 can incorporate a groove 324 along the top thereof to guide and partially sheath blade 320 therein as best seen in FIG. 3B. This also prevents blade 320 from presenting itself as a source of injury when jaw assembly 30 is closed.

In operation, with jaws 302 and 304 in their open position as shown in FIG. 3A, clamp 20 is seated therein by placing recessed portion 218 of clamp 20 over positioning anvil 322 which is shaped to mate with recessed portion 218. To further aid in the retaining of clamp 20 in its open position, upper jaw 302 can incorporate a lip 302A at its outboard end thereof. In this open position, cutting blade 320 resides above clamp 20 (FIG. 1). Positioning anvil 322 aligns clamp 20 such that groove 220 is aligned with blade 320. The compressible structure, e.g., umbilical cord 100, to be severed is placed between arms 202 and 204. Handles 306 and 308 are then squeezed by an individual applying a gripping force. As handles 306 and 308 are squeezed, jaws 302 and 304 apply a compressive force to arms 202 and 204 until latching tangs 210A and 210B seat in latching seats 212A and 212B, respectively. At this point, clamp 20 is in its clamped position with ridges 203 and 205 tending to interlock with umbilical cord 100 being fully compressed therebetween. More specifically, the portion of umbilical cord 100 passing through clamp 20 has all of its contained blood and other fluids (not shown) pushed outward to either side of clamp 20. When clamp 20 is in its clamped position (i.e., closed and latched), the height of blade 320 is such that it has not yet encountered the reduced thickness portion of clamp 20 between the groove 220 and ridges 203. However, as handles 306 and 308 are continually squeezed together, blade 320 cuts through arm 202 at its reduced thickness portion 221, umbilical cord 100, and arm 204 at its reduced thickness portion 219.

Since clamp 20 is held laterally in jaw assembly 30 only by anvil 322, clamp 20 is free to move laterally away from jaw assembly 30 as it is severed into to clamps 21 and 22 as shown in FIG. 4. That is, clamp 21 remains clamped, via latching tang 210A and latching seat 212A, onto one severed end of umbilical cord 100. Similarly clamp 22 remains clamped, via latching tang 210B and latching seat 212B, onto the other severed end of umbilical cord 100. Since there were no fluids present in the severed portion of umbilical cord 100, there are no fluids to be discharged into the surrounding environment.

The advantages of the present invention are numerous. The device allows a fluid-filled compressible structure to be severed without fluid discharge. The device itself remains bloodless thereby also eliminating the possibility that someone will be contaminated by simply touching the device. Further, the clamping and cutting operations are conveniently accomplished with a single motion thereby allowing the operation to be performed quickly. The device can be made as a completely disposable or reusable item for use in surgical procedures. In the illustrated embodiment, the jaw assembly need not be oriented specially for either left or right-handed individuals and is therefore a multi-directional tool. The device's simplicity of operation means that even a non-professional could use the device effectively.

Figure 5:
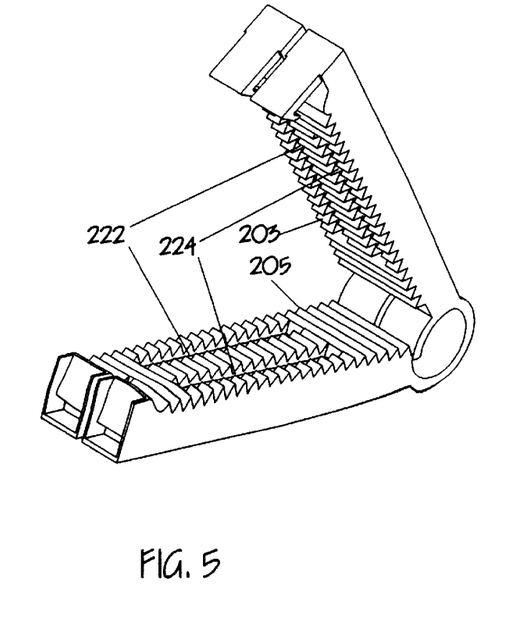
FIG. 5 is a perspective view of another embodiment of a clamp that can be used in the present invention.

Although the invention has been described relative to a specific embodiment thereof, there are numerous variations and modifications that will be readily apparent to those skilled in the art in light of the above teachings. For example, ridges 203 and 205 could be eliminated or replaced with any type of serration, teeth or other structure as dictated by the particular application. Another possibility is to provide grooves that cut across the ridges in order to prevent a compressible structure from slipping through the clamp. This is illustrated in FIG. 5 where grooves 222 and 224 cut perpendicularly across ridges 203 and 205 on either side of the area of clamp 20 that will be severed. In this way, as clamp 20 is placed in its clamped position, the compressible structure is captured in grooves 222 and 224 to prevent it from slipping in a direction perpendicular thereto.

In other alternatives, the clamp itself need not be hinged together but could be formed of two separate mating pieces that can be latched together. In some applications, the clamp could be positioned and clamped in one operation and then severed by a separate cutting means in another operation. With respect to the jaw assembly, the linkages thereof can be altered to give more or less mechanical advantage as needed. Alternative and/or additional positioners can be provided on the jaw assembly (i.e., instead of or in addition to anvil 322) to seat the clamp. The blade shape and/or configuration can be altered to assure proper sequencing of the clamping and cutting operations. Proper sequencing could also be aided by adding material to the clamp at strategic locations to prevent premature cutting of the clamp. The jaw assembly could also incorporate a separate clamping mechanism that operated just prior to a separate cutting mechanism. It is therefore to be understood that, within the scope of the appended claims, the invention may be practiced other than as specifically described.

What is claimed as new and desired to be secured by Letters Patent of the United States is:

1. A device for clamping and severing a compressible structure containing a fluid, comprising:

a clamp having a pair of arms securable in a clamped position about a compressible structure containing a fluid wherein said fluid in said compressible structure between said arms is forced outward from said clamp; and a cutting assembly coupled to said clamp for cutting through said pair of arms while in said clamped position to form first and second separated clamps that remain in said clamped position wherein said compressible structure is severed to form first and second severed ends thereof with said first and second ends being clamped by a respective one of said first and second separated clamps.

2. A device as in claim 1 wherein said pair of arms include ridges that interlock when said clamp is in said clamped position.

3. A device as in claim 2 wherein said pair of arms further include at least one groove formed in said ridges in areas of said pair of arms that will become each of said first and second separated clamps, said at least one groove running substantially perpendicular to said ridges.

4. A device as in claim 1 further comprising first and second latches coupled to said clamp for securing said clamp in said clamped position, said first and second latches maintained in a spaced-apart relation to one another wherein said first latch remains with said first separated clamp and said second latch remains with said second separated clamp.

5. A device as in claim 1 further comprising a hinge for hingedly coupling said pair of arms to one another.

6. A device as in claim 5 wherein said hinge includes a limit stop for preventing said compressible structure from interfering with said hinge.

7. A device as in claim 5 wherein said hinge comprises first and second hinges maintained in a spaced-apart relation to one another wherein said first hinge remains with said first separated clamp and said second hinge remains with said second separated clamp.

8. A device as in claim 1 wherein said cutting assembly comprises:

a pair of jaws for supporting said clamp prior to being placed in said clamped position and in said clamped position, and for releasing said first and second separated clamps in said clamped position; and a cutting blade mounted on a first of said pair of jaws wherein, when a compressive force is supplied to said pair of jaws, said clamp is forced into said clamped position and said cutting blade is brought to bear against said clamp in said clamped position, and wherein said cutting blade cuts through said pair of arms in said clamped position as said compressive force is continually applied.

9. A device as in claim 8 further comprising at least one positioner coupled to said pair of jaws for properly positioning said clamp in said pair of jaws relative to said cutting blade.

10. A device as in claim 9 wherein a backside of one of said pair of arms includes a recessed portion, and wherein said at least one positioner comprises a projection coupled to a second of said pair of jaws such that said projection seats in said recessed portion when said clamp is supported in said pair of jaws.

11. A device as in claim 10 wherein said projection opposes said cutting blade substantially therealong to form an anvil upon which said cutting blade comes to rest after said cutting blade cuts through said pair of arms.

12. A device as in claim 11 wherein said anvil has a groove formed therein for at least partially sheathing said cutting blade after said cutting blade cuts through said pair of arms.

13. A device as in claim 8 wherein said clamp in said clamped position defines a reduced thickness portion for facilitating the severing thereof by said cutting blade.

14. A device for clamping and severing a compressible structure containing a fluid, comprising:
a clamp having a pair of arms coupled with a hinge for allowing relative motion between said pair of arms, said pair of arms including a latch for securing said pair of arms in a clamped position about a compressible structure containing a fluid wherein said fluid in said compressible structure between said arms is forced outward from said clamp;
a pair of jaws having a cutting blade mounted on one of said pair of jaws, said pair of jaws supporting said clamp prior to being placed in said clamped position and in said clamped position; and
a handle assembly coupled to said pair of jaws operable to supply a compressive force to said pair of jaws wherein said clamp is forced into said clamped position and said cutting blade is brought to bear against said clamp in said clamped position, and wherein said cutting blade cuts through said pair of arms in said clamped position as said compressive force is continually applied to form first and second separated clamps that remain in said clamped position wherein said compressible structure is severed to form first and second severed ends thereof with said first and second ends being clamped by a respective one of said first and second separated clamps.

15. A device as in claim 14 wherein said pair of arms include interlocking ridges that run parallel to said compressible structure when said clamp is in said clamped position, said interlocking ridges spanning at least the width of said compressible structure.

16. A device as in claim 15 wherein said pair of arms further include at least one groove formed in said ridges in areas of said pair of arms that will become each of said first and second separated clamps, said at least one groove running substantially perpendicular to said ridges.

17. A device as in claim 14 wherein:
said latch comprises first and second latches coupled to said clamp for securing said clamp in said clamped position, said first and second latches maintained in a spaced-apart relation to one another wherein said first latch remains with said first separated clamp and said second latch remains with said second separated clamp; and
said hinge comprises first and second hinges maintained in a spaced-apart relation to one another wherein said first hinge remains with said first separated clamp and said second hinge remains with said second separated clamp.

18. A device as in claim 17 wherein said clamp in said clamped position defines a reduced thickness portion between said hinge and said latch for facilitating the severing of said pair of arms in said clamped position by said cutting blade.

19. A device as in claim 14 further comprising at least one positioner coupled to said pair of jaws for properly positioning said clamp in said pair of jaws relative to said cutting blade.

20. A device as in claim 19 wherein a backside of one of said pair of arms includes a recessed portion, and wherein said at least one positioner comprises a projection coupled to a second of said pair of jaws such that said projection seats in said recessed portion when said clamp is supported in said pair of jaws.

21. A device as in claim 20 wherein said projection opposes said cutting blade substantially therealong to form an anvil upon which said cutting blade comes to rest after said cutting blade cuts through said pair of arms.

22. A device as in claim 21 wherein said anvil has a groove formed therein for at least partially sheathing said cutting blade after said cutting blade cuts through said pair of arms.

23. A device as in claim 14 wherein said hinge includes a limit stop for preventing said compressible structure from interfering with said hinge.

24. A method of clamping and severing a compressible structure containing a fluid, comprising the steps of:
providing a clamp having a pair of arms securable in a clamped position;
placing said clamp in said clamped position about a periphery of a compressible structure containing a fluid wherein said fluid in said compressible structure between said pair of arms is forced outward from said clamp; and
severing said pair of arms in said clamped position about said periphery of said compressible structure along with said compressible structure in a single plane to thereby form first and second separated clamps that remain in said clamped position wherein said compressible structure is severed in said single plane to form first and second severed ends thereof with said first and second ends being clamped by a respective one of said first and second separated clamps.

25. A method according to claim 24 wherein said step of placing comprises the steps of:
providing a pair of jaws that support said clamp both prior to being placed in said clamped position and in said clamped position, and that release said first and second separated clamps in said clamped position;
providing a cutting blade mounted on a first of said pair of jaws; and
applying a compressive force to said pair of jaws to force said clamp into said clamped position.

26. A method according to claim 25 wherein said step of severing is accomplished by continuing said step of applying so that said cutting blade is brought to bear against said clamp in said clamped position and said cutting blade cuts through said pair of arms in said clamped position.

27. A method according to claim 26 wherein said step of applying is accomplished by the gripping force of an individual.

* * * * *